(12) United States Patent
Chapman et al.

(10) Patent No.: US 8,331,678 B2
(45) Date of Patent: Dec. 11, 2012

(54) SYSTEMS AND METHODS FOR IDENTIFYING A DISCONTINUITY IN THE BOUNDARY OF AN OBJECT IN AN IMAGE

(75) Inventors: Kenneth Wayne Chapman, Raleigh, NC (US); Prasant Potuluri, Raleigh, NC (US)

(73) Assignee: Optopo Inc., Morrisville, NC (US)

(*) Notice: Subject to any disclaimer, the term of this patent is extended or adjusted under 35 U.S.C. 154(b) by 332 days.

(21) Appl. No.: 12/839,366

(22) Filed: Jul. 19, 2010

(65) Prior Publication Data

US 2010/0278382 A1 Nov. 4, 2010

Related U.S. Application Data

(63) Continuation-in-part of application No. 12/326,558, filed on Dec. 2, 2008, which is a continuation-in-part of application No. 11/609,443, filed on Dec. 12, 2006, now Pat. No. 7,720,694, which is a continuation-in-part of application No. 11/454,923, filed on Jun. 19, 2006, now Pat. No. 7,218,395.

(60) Provisional application No. 60/725,311, filed on Oct. 12, 2005, provisional application No. 60/811,101, filed on Jun. 6, 2006.

(51) Int. Cl.
  *G06K 9/00* (2006.01)
(52) U.S. Cl. .......... 382/181; 348/92; 356/239.6; 702/84
(58) Field of Classification Search .......... 382/100, 382/103, 181, 190, 195, 199, 203, 206, 224, 382/254, 256, 257, 258, 259, 266; 348/92, 348/135, 169–172; 702/81, 84; 356/237.1, 356/239.5, 239.6
See application file for complete search history.

(56) References Cited

U.S. PATENT DOCUMENTS

| | | | | |
|---|---|---|---|---|
| 5,189,711 | A * | 2/1993 | Weiss et al. | 382/203 |
| 5,864,395 | A * | 1/1999 | Laurberg | 356/239.6 |
| 6,535,637 | B1 * | 3/2003 | Wootton et al. | 382/190 |
| 7,399,968 | B2 | 7/2008 | Lewis et al. | |
| 2002/0009218 | A1 | 1/2002 | Chapman et al. | |
| 2003/0214649 | A1 * | 11/2003 | Yagita | 356/239.5 |
| 2004/0207842 | A1 | 10/2004 | Rzasa et al. | |
| 2005/0276443 | A1 * | 12/2005 | Slamani et al. | 382/103 |
| 2005/0288906 | A1 | 12/2005 | Drennen, III et al. | |
| 2007/0260487 | A1 | 11/2007 | Bartfeld et al. | |
| 2009/0154764 | A1 * | 6/2009 | Khan et al. | 382/100 |
| 2010/0232640 | A1 * | 9/2010 | Friend et al. | 382/100 |
| 2011/0123077 | A1 * | 5/2011 | Goto | 382/128 |

* cited by examiner

*Primary Examiner* — Anand Bhatnagar
(74) *Attorney, Agent, or Firm* — John R. Kasha; Kasha Law LLC

(57) ABSTRACT

Machine vision is used to identify a discontinuity in the boundary of an object in an image. An image of one or more objects is captured. One or more skeletons of the one or more objects are calculated. One or more boundaries of the one or more objects are calculated. A plurality of radial lines is extended from a spine point of a skeleton to the one or more boundaries. Each radial line intersects a boundary at a radial endpoint producing a plurality of radial endpoints. For each radial endpoint an expected radial endpoint is calculated based on two or more neighboring radial endpoints. If the difference between the radial endpoint and its expected radial endpoint exceeds a threshold, a radial line including the radial endpoint is identified as a discontinuity in a boundary of an object.

20 Claims, 14 Drawing Sheets

US 8,331,678 B2

SYSTEMS AND METHODS FOR IDENTIFYING A DISCONTINUITY IN THE BOUNDARY OF AN OBJECT IN AN IMAGE

CROSS-REFERENCE TO RELATED APPLICATION

This application is a continuation-in-part application of U.S. patent application Ser. No. 12/326,558, filed Dec. 2, 2008 (the "'558 application"). The '558 application is a continuation-in-part application of U.S. patent application Ser. No. 11/609,443, filed Dec. 12, 2006 now U.S. Pat. No. 7,720, 694 (the "'443 application"). The '443 application is a continuation-in-part application of U.S. patent application Ser. No. 11/454,923 (the "'923 application"), filed Jun. 19, 2006 now U.S. Pat. No. 7,218,395 (the "'395 patent"). The '923 application claims the benefit of U.S. Provisional Patent Application No. 60/725,311, filed Oct. 12, 2005, and U.S. Provisional Patent Application No. 60/811,101, filed Jun. 6, 2006. All of the above mentioned applications are incorporated by reference herein in their entireties.

INTRODUCTION

Generally, the pills or capsules used to hold prescription pharmaceuticals have shapes and colors that uniquely identify the pharmaceutical and its strength. These shapes and colors are used by pharmacists to verify that the dispensed pharmaceuticals match the prescription.

Automated pharmacy verification systems can also verify dispensed pharmaceuticals by shape and color. These systems typically include a light source for illuminating the dispensed pills or capsules and an imaging device for obtaining an image of the dispensed pills or capsules. A computer or processor is then used to identify the shape and color of the pills or capsules from the image. The shape and color of the pills or capsules are identified from the image using image processing algorithms. These image processing algorithms and the hardware used to capture the image are collectively referred to as "machine vision."

Traditional automated pharmacy verification systems use machine vision to determine if an isolated capsule or pill in an image matches a known shape and color. Often, however, all the capsules or pills in an image are obscured by each other or by an artifact of their container. As a result, an isolated capsule or pill is not available in the image. Also, a priori information about a known shape is not available. As a result, all possible shapes and colors have to be searched, which can be too computationally expensive for a real-time system.

Figure 1:
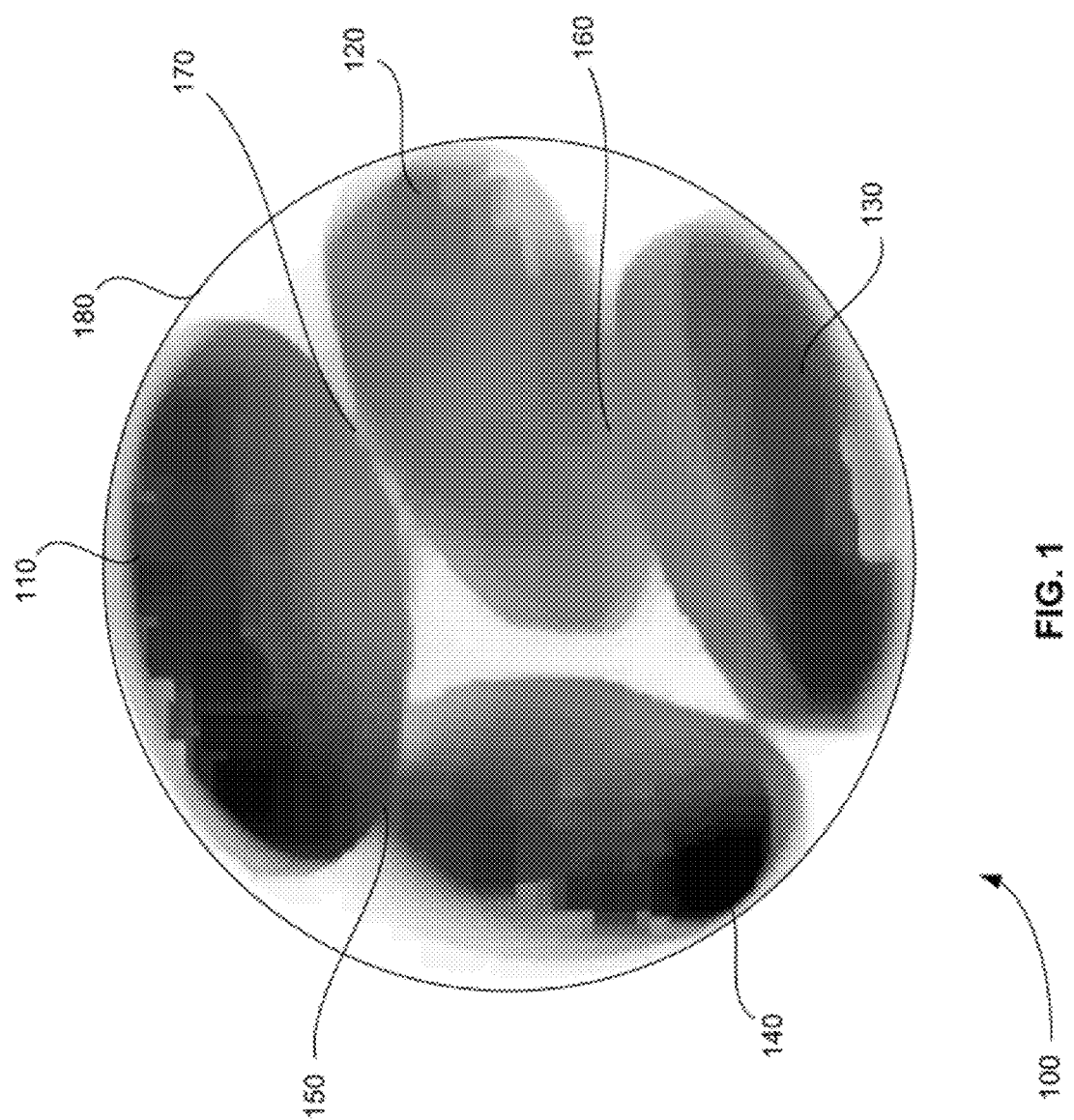
FIG. 1 is an exemplary negative captured image of the bottom of a prescription vial that contains pills of a prescribed pharmaceutical, in accordance with various embodiments.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION

Methods for identifying a pharmaceutical solid in a prescription vial using machine vision are described in the '558 application. In one method, a pharmaceutical solid in a prescription vial is identified from the shape of the pharmaceutical solid using light reflected from two different light sources. Shapes corresponding to known pharmaceutical solids are stored. The prescription vial is illuminated with a first light source and a first image is recorded. The prescription vial is then illuminated with a second light source and a second image is recorded. The first image and the second image are processed to find a shape of the pharmaceutical solid. The shape found is compared to one or more of the stored shapes. The identity of the pharmaceutical solid is determined from the comparison.

In another method, a pharmaceutical solid in a prescription vial is identified from an optical property of the pharmaceutical solid using two light sources that effectively remove artifacts of the prescription vial. For each known pharmaceutical solid, an optical property of the known pharmaceutical solid is stored. The optical property can include, but is not limited to, a shape, a color, a geometric engraving, or a coplanar symbol. The prescription vial is illuminated with a first light source that is substantially transmitted by artifacts of the prescription vial and a first image is recorded. The prescription vial is then illuminated with a second light source that is substantially reflected by the artifacts and a second image is recorded. The second image is used to remove the effects of the artifacts in the first image and the first image is processed to find the optical property of the pharmaceutical solid. The optical property is compared to the stored optical properties that identify known pharmaceutical solids. The pharmaceutical solid is identified from this comparison.

In another method, a pharmaceutical solid in a prescription vial is identified from an optical property using directional lighting to enhance or suppress two-dimensional or three-dimensional effects on the surface of the pharmaceutical solid. As above, for each known pharmaceutical solid, an optical property of the known pharmaceutical solid is stored. A first direction and a second direction are selected. The prescription vial is illuminated with a light from the first direction and a first image is recorded. The prescription vial is then illuminated with the light from the second direction and a second image is recorded. The first image and the second image are processed to find an optical property of the pharmaceutical solid. The optical property is compared to the stored optical properties that identify known pharmaceutical solids. The pharmaceutical solid is identified from this comparison.

In another method, a pharmaceutical solid in a prescription vial is identified from an optical property of the pharmaceutical solid using one light source that includes a light frequency that effectively allows artifacts of the prescription vial to be removed. As above, for each known pharmaceutical solid, an optical property of the known pharmaceutical solid is stored. The prescription vial is illuminated with a light source that includes a light frequency that is substantially reflected by artifacts of the prescription vial. An image is recorded. Edges recorded in the image from the light frequency are used to remove the effects of the artifacts in the image and the image is processed to find an optical property of the pharmaceutical solid. A first comparison of the optical property to one or more of the plurality of stored known optical properties is performed. The identity of the pharmaceutical solid is determined from the first comparison.

A system for communicating pharmaceutical verification information across a network is described in the '443 application. This pharmaceutical verification information includes at least one known spectral signature of a known pharmaceutical that is sent to an automatic prescription verification system across the network.

An automatic prescription verification system that uses spectroscopic analysis is described in the '395 patent. A system of the '395 patent uses a static multimode multiplex spectrometer (MMS).

According to a system of the '395 patent, a standard prescription bottle or vial containing a pharmaceutical of a prescription is placed in a spectroscopic sensor system. The spectroscopic sensor system excites the Raman-active modes of the pharmaceutical and detects the resulting Raman emission. A spectral signature that is derived from the measurement is compared to one or more spectral signatures of known pharmaceuticals that are stored in a database. If the spectral signature of the pharmaceutical in the vial matches a spectral signature of a known pharmaceutical stored in the database, the pharmaceutical in the vial is identified. If the identity of the pharmaceutical in the vial matches the pharmaceutical of the prescription, the prescription is verified.

A system of the '395 patent may also include an imaging device to assist in uniquely identifying the pharmaceutical in the prescription vial. The spectral and imaging database may contain images of pharmaceuticals showing their size, shape, color and/or texture, or other data characterizing the size, shape, color and/or texture of known pharmaceuticals. For example, certain pharmaceutical tablets are provided in different sizes according to the strength of the pharmaceutical. In these cases, different strengths of the same pharmaceutical may have the same spectral signature, such that the spectral signature cannot be used to identify the strength in addition to identifying the pharmaceutical itself. Once the pharmaceutical has been identified, the imaging device can then be used to identify the strength by comparing the size of the prescription tablet to the sizes for different strengths of that pharmaceutical in the spectral and image database. The imaging device can also be used to determine the shape and/or color of the tablets. This data can then be used as a double-check on the identity of the pharmaceutical, or to differentiate between different strengths or forms (tablets, caplets, liquids, pills, capsules, etc.) of the pharmaceuticals.

Embodiments of the present invention include systems and methods for identifying the shape of an object in an image when that object is touching another object or is partially occluded by another object, the container enclosing the object, or other artifacts in the image.

Identification of Merged or Occluded Shapes

As described above, traditional automated pharmacy verification systems can use machine vision to determine the identity of a prescribed pharmaceutical from the shape and color of a capsule or pill. However, these systems do not perform well if the capsules or pills appear to be in contact or merged with each other, or if the capsules or pills are occluded by other capsules or pills, a container, or other artifacts that are part of the captured image. Also, these systems do not perform well if some a priori information about the shape or color of capsules or pills being analyzed is not available.

In various embodiments, machine vision is used to identify the shape and color of an object that is merged with another object or occluded by another object, a container, or some other artifact in the image and without any a priori information about the shape and color of the object. Although the following description pertains to identifying the shape and color of capsules or pills in a prescription vial, one skilled in that art can appreciate that the systems and methods described can similarly be applied to any object that is merged with another object or occluded by another object or artifact in a captured image. Some non-limiting examples include fruit or vegetables traveling down a conveyor belt, nuts and washers in a jar, bacteria growing in a Petri dish, or particles such as sand or leaves in water or other liquids.

FIG. 1 is an exemplary negative captured image 100 of the bottom of a prescription vial 180 that contains pills of a prescribed pharmaceutical, in accordance with various embodiments. In captured image 100, pills 110, 120, 130, and 140 are apparent. Pill 140 appears to be occluded by pill 110 or is merged with pill 110 at location 150. Similarly, pill 120 appears to be occluded by pill 130 or is merged with pill 130 at location 160. In addition, pill 110 and pill 120 appear to merge at location 170 due to an artifact of the prescription vial 180. Artifacts of the prescription vial 180 can include, but are not limited to, writing embossed in the bottom of the vial or circular indentations in the bottom of the vial.

In various embodiments, the shape of a merged or occluded pill is reconstructed from a skeleton and a boundary image of the original captured image. A skeleton image depicts the spines of objects in a captured image. Spines are points equidistant from the boundaries of each object. A boundary image depicts the boundaries of each object in the captured image.

Figure 2:
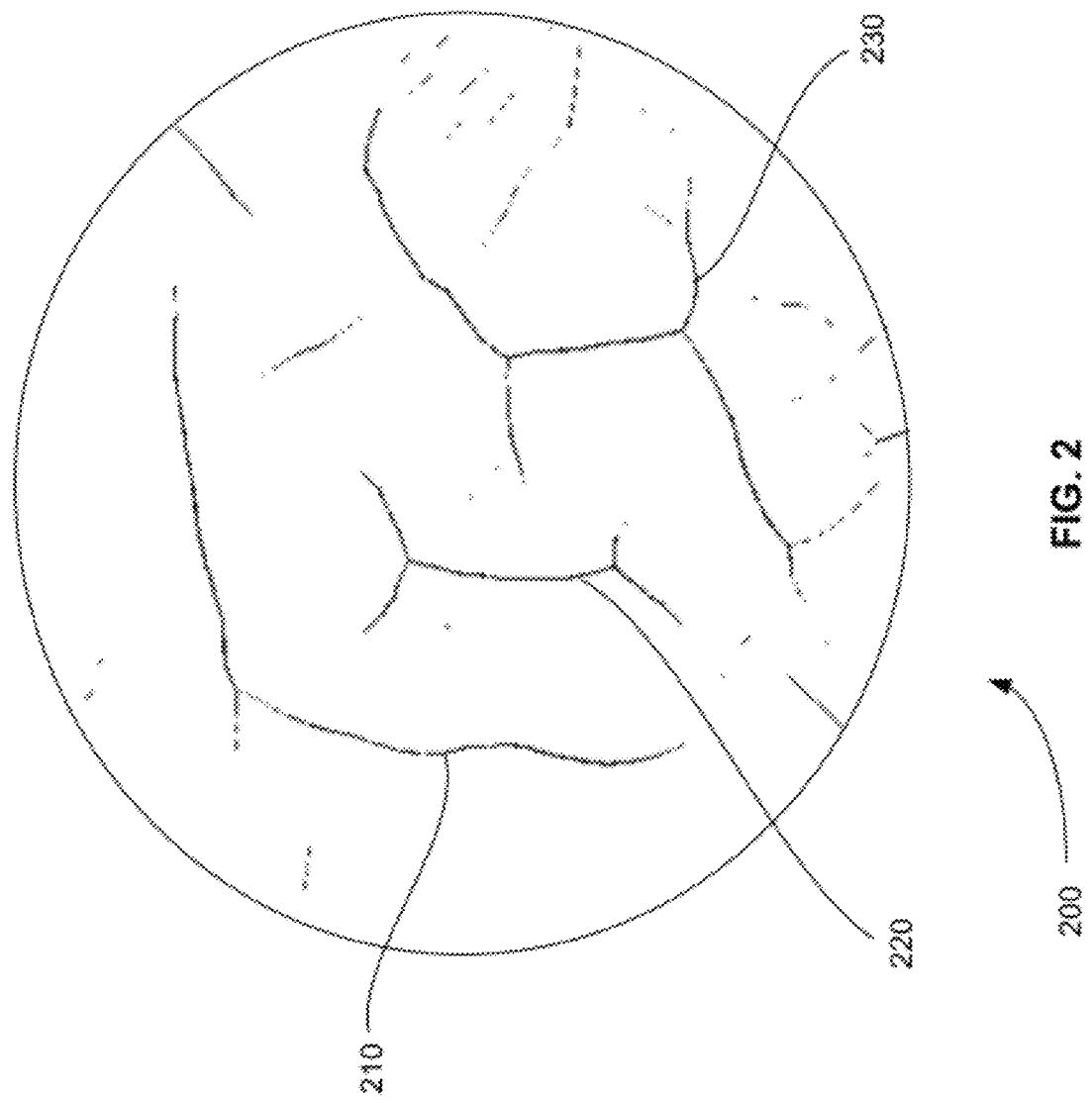
FIG. 2 is an exemplary skeleton image of the captured image shown in FIG. 1, in accordance with various embodiments.

FIG. 2 is an exemplary skeleton image 200 of the captured image shown in FIG. 1, in accordance with various embodiments. Spines 210, 220, and 230 are most apparent in skeleton image 200, although many other spines are also shown. A spine is formed for any body of continuous homogenously colored pixels. A skeleton image, such as skeleton image 200, can be created using a distance transform or a mathematical morphology, for example.

Spines are formed for both pills and areas between pills. Spine 210 extends from pill 110 of FIG. 1, through merged location 150 of FIG. 1, to pill 140 of FIG. 1. Spine 230 of FIG. 2 extends from pill 120 of FIG. 1, through merged location 170 of FIG. 1, to pill 130 of FIG. 1. Spine 220 of FIG. 2 is formed in the area between pills 110, 120, 130, and 140 of FIG. 1.

Figure 3:
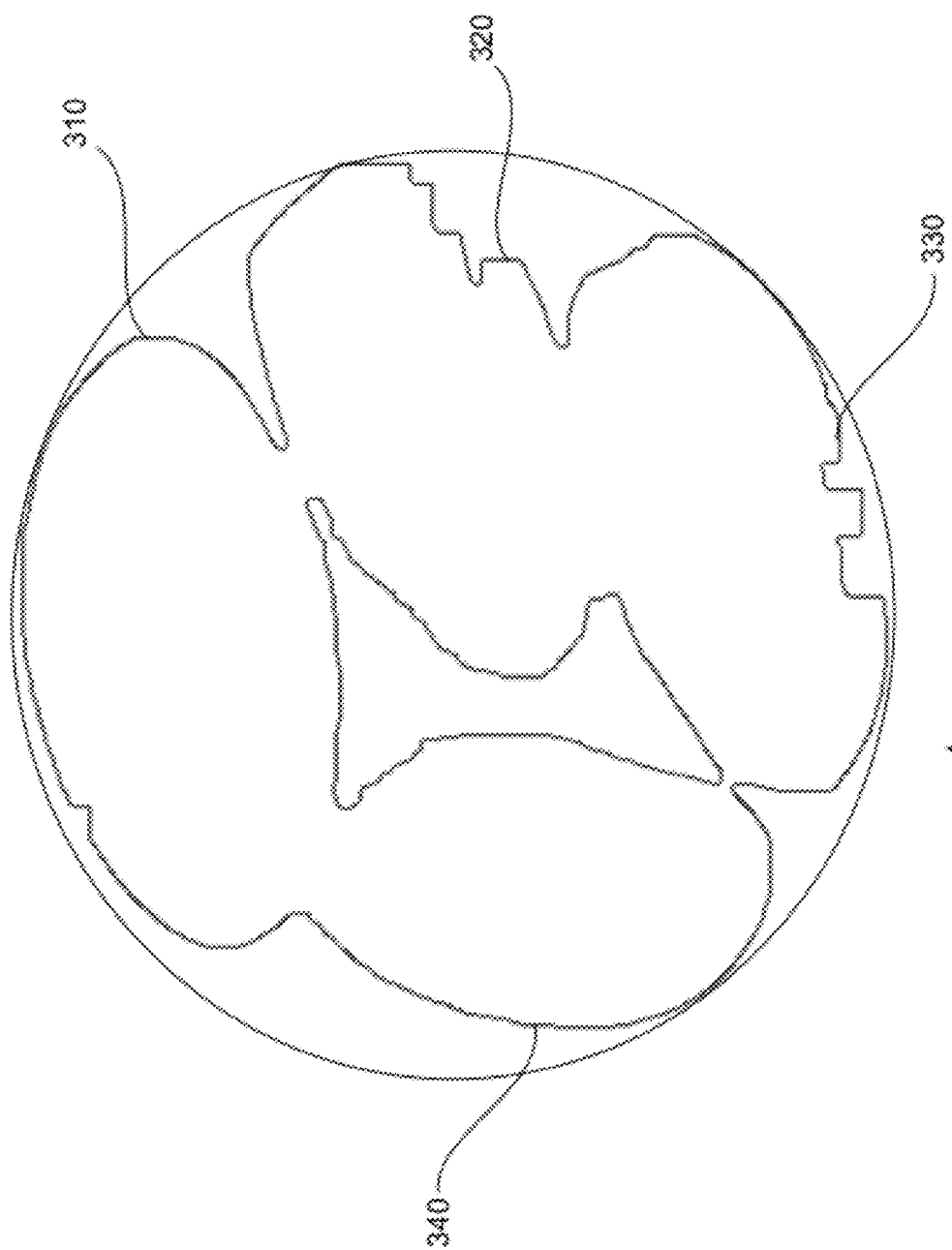
FIG. 3 is an exemplary boundary image of the captured image shown in FIG. 1, in accordance with various embodiments.

FIG. 3 is an exemplary boundary image 300 of the captured image shown in FIG. 1, in accordance with various embodiments. Boundaries 310, 320, 330, and 340 are shown in boundary image 300. A boundary is formed where significant transitions in color take place. A boundary image, such as boundary image 300, can be created using an edge detection algorithm, for example. Edge detection algorithms can include, but are not limited to, Canny, Sobel, Roberts, or a mathematical morphology. Boundaries 310, 320, 330, and 340 correspond substantially to pills 110, 120, 130, and 140 of FIG. 1.

Figure 4:
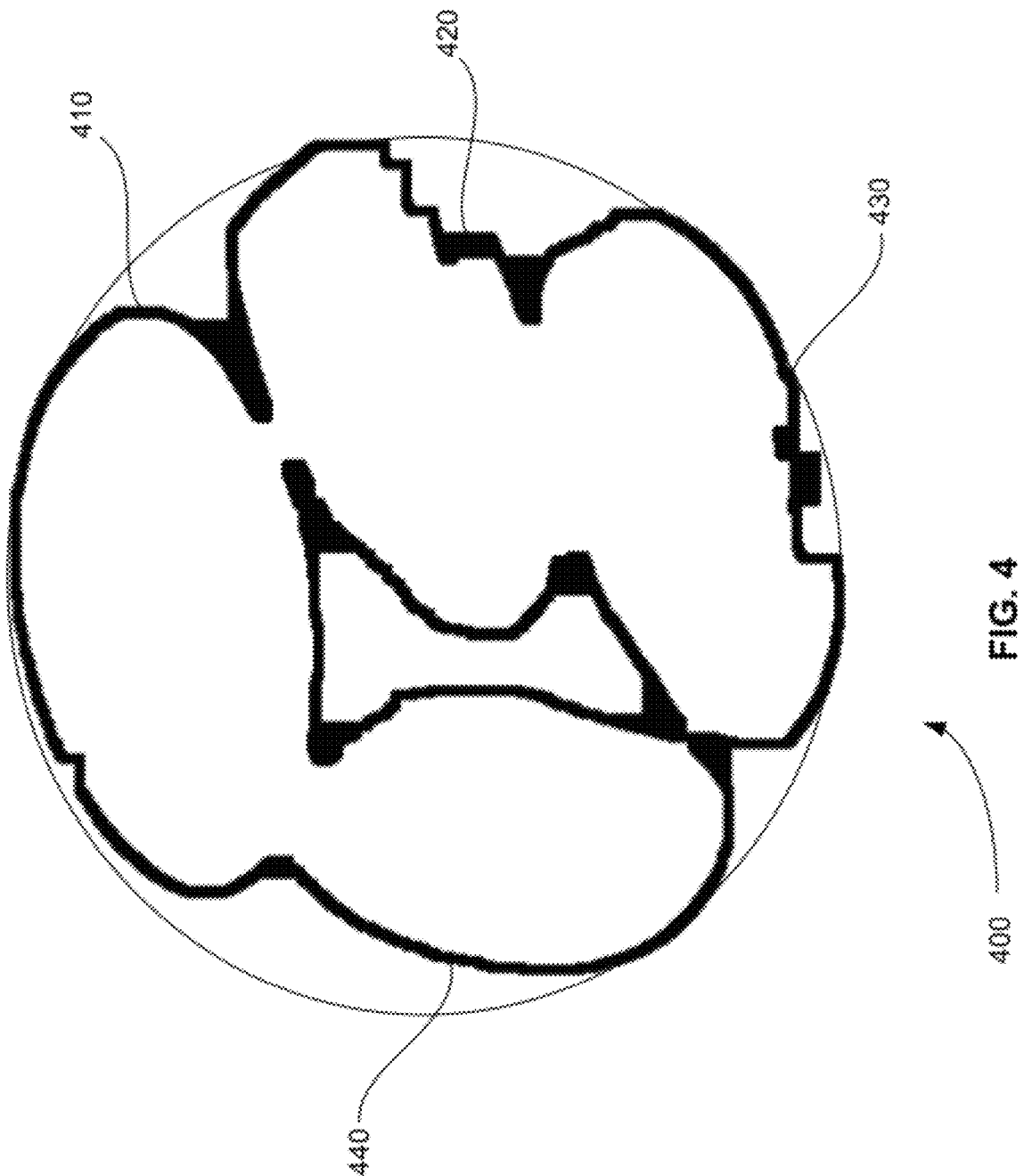
FIG. 4 is an exemplary dilated image of the boundary image shown in FIG. 3, in accordance with various embodiments.

FIG. 4 is an exemplary dilated image 400 of the boundary image shown in FIG. 3, in accordance with various embodiments. Boundaries 410, 420, 430, and 440 are shown in dilated image 400. Boundaries 410, 420, 430, and 440 are produced by thickening or dilating boundaries 310, 320, 330, and 340 of FIG. 3. The boundaries of FIG. 3 are dilated using a mathematical morphology algorithm, for example. These boundaries are dilated and image 400 of Figure is created to shrink the areas of discontinuity. These areas of discontinuity are the merged or occluded boundary areas, for example.

Figure 5:
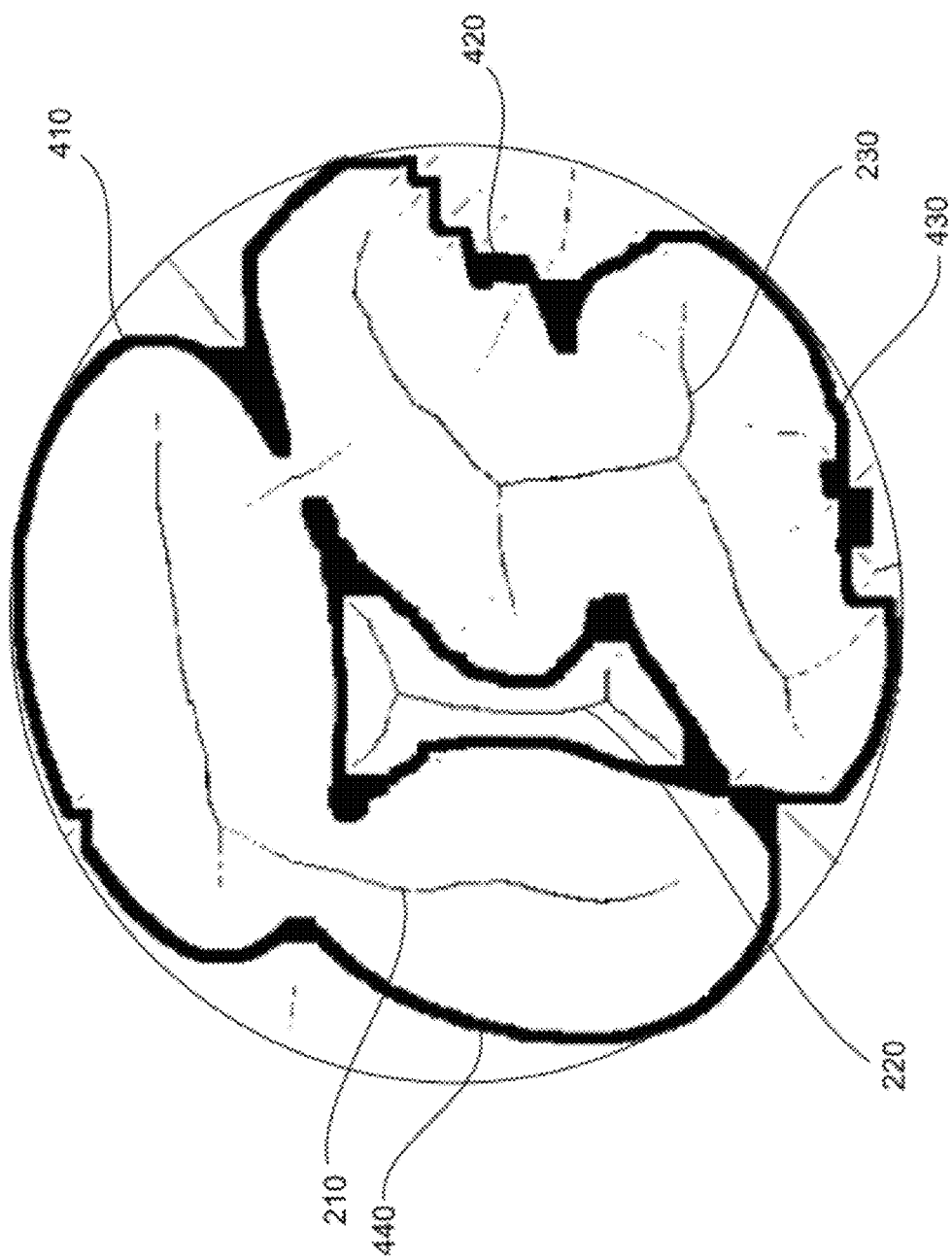
FIG. 5 is an exemplary combined image of the skeleton image of FIG. 2 and the dilated image of FIG. 4, in accordance with various embodiments.

FIG. 5 is an exemplary combined image 500 of the skeleton image of FIG. 2 and the dilated image of FIG. 4, in accordance with various embodiments. Combined image 500 includes spines 210, 220, and 230 and boundaries 410, 420, 430, and 440. Combined image 500 is shown for illustrative purposes. Skeleton image 200 of FIG. 2 and the dilated image 400 of FIG. 4 can be created, stored, and analyzed separately, for example.

In various embodiments, the shape of a merged or occluded pill is reconstructed for each spine point of the pill by dividing the area between the spine point and its boundaries into a large number of small triangular slices. The triangular slices are created by extending a number of lines radially from the spine point until each of the lines reaches a boundary of the spine point. The lines are preferably extended at evenly spaced radial angles. In various embodiments, the lines can be extended at unevenly spaced radial angles.

Each radial line extended from the spine point intersects a boundary at a radial endpoint of the line. An expected radial endpoint is calculated for each radial line based on two or more actual preceding radial endpoints, two or more actual following radial endpoints, or both two or more actual preceding radial endpoints and two or more actual following radial endpoints. An expected radial endpoint is calculated using a curve fitting algorithm, for example.

Merged or occluded areas are identified by comparing each expected radial endpoint with the actual radial endpoint. If the difference in lengths from the spine point to expected radial endpoint and from the spine point to actual radial endpoint exceeds a certain threshold, for example, a discontinuity is found. This discontinuity identifies a potential merged or occluded area.

One or more of the following steps can be executed to attempt to reconstruct the pill shape in a merged or occluded area. In one step, one or more radial lines are added closer to the radial line that identifies the merged or occluded area to provide closer neighboring endpoints. In another step, the closest neighboring endpoints are replaced by one or more radial lines added further from or closer to the radial line that identifies the merged or occluded area. In another step, the radial line that identifies the merged or occluded area is simply ignored. In another step, the expected radial endpoint of the radial line that identifies the merged or occluded area is recalculated using the next nearest neighboring actual endpoints rather than the nearest neighboring actual endpoints.

Figure 6:
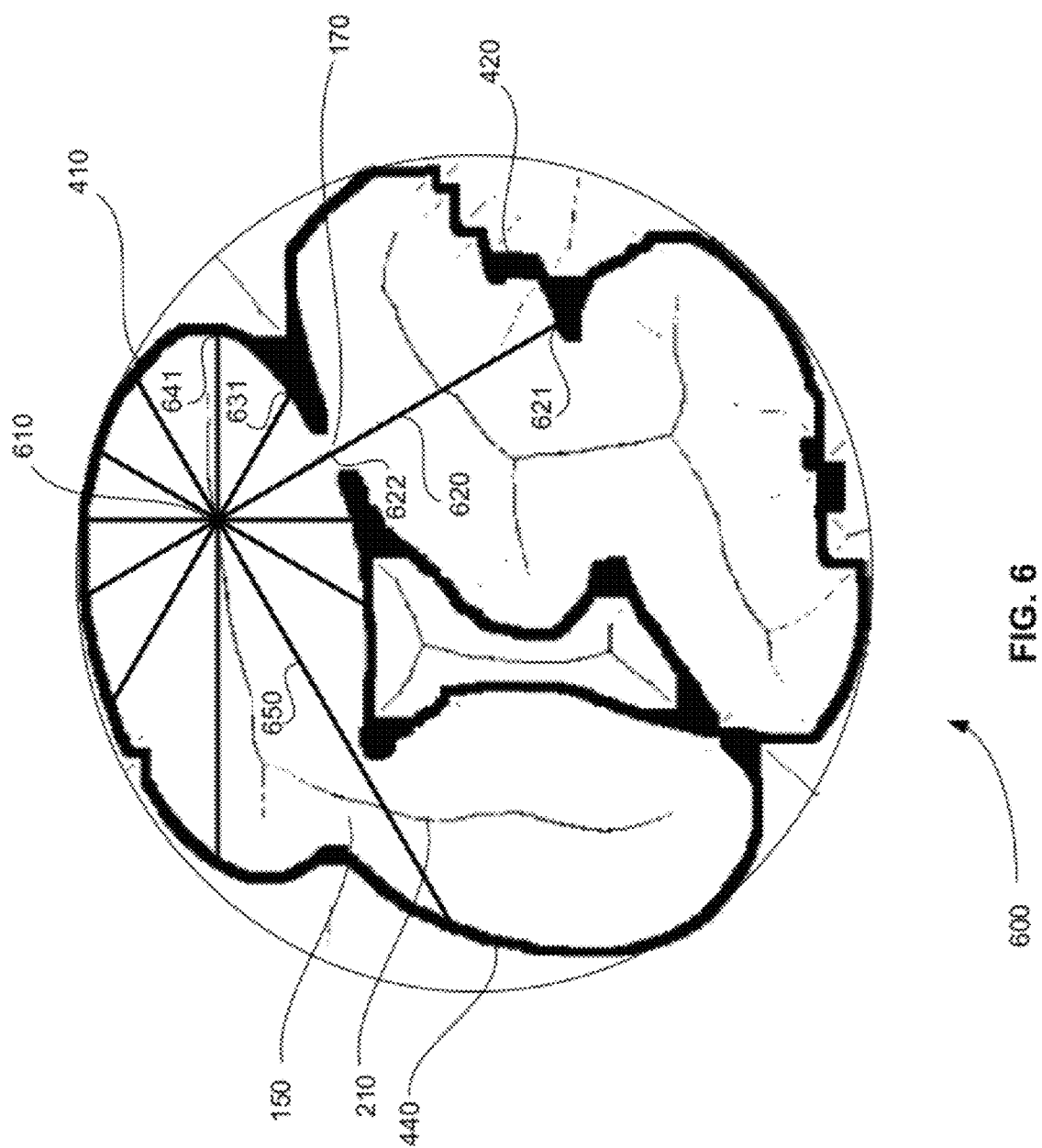
FIG. 6 is an exemplary combined image of the skeleton image of FIG. 2 and the dilated image of FIG. 4 that includes twelve radial lines extending from a spine point to a boundary, in accordance with various embodiments.

FIG. 6 is an exemplary combined image 600 of the skeleton image of FIG. 2 and the dilated image of FIG. 4 that includes twelve radial lines extending from a spine point 610 to a boundary, in accordance with various embodiments. The twelve radial lines are extended from spine point 610 of spine 210 and are evenly spaced 30 degrees apart. The majority of the twelve radial lines are extended to boundary 410. Radial line 620 extends to boundary 420 and radial line 650 extends to boundary 440, however.

An expected radial endpoint is calculated for each of the twelve radial lines in combined image 600 based on two or more actual preceding radial endpoints. For example, if the expected radial endpoints are calculated in a clockwise fashion, expected radial endpoint 622 is calculated for radial line 620 from actual radial endpoints 631 and 641. The difference in lengths from spine point 610 to expected radial endpoint 622 and from the spine point to actual radial endpoint 621 exceeds a threshold and identifies a merged or occluded area, for example. In fact, it identifies occluded area 170, as also shown in FIG. 1. Similarly, radial line 650 of FIG. 6 is found to identify merged area 150, as also shown in FIG. 1.

Figure 7:
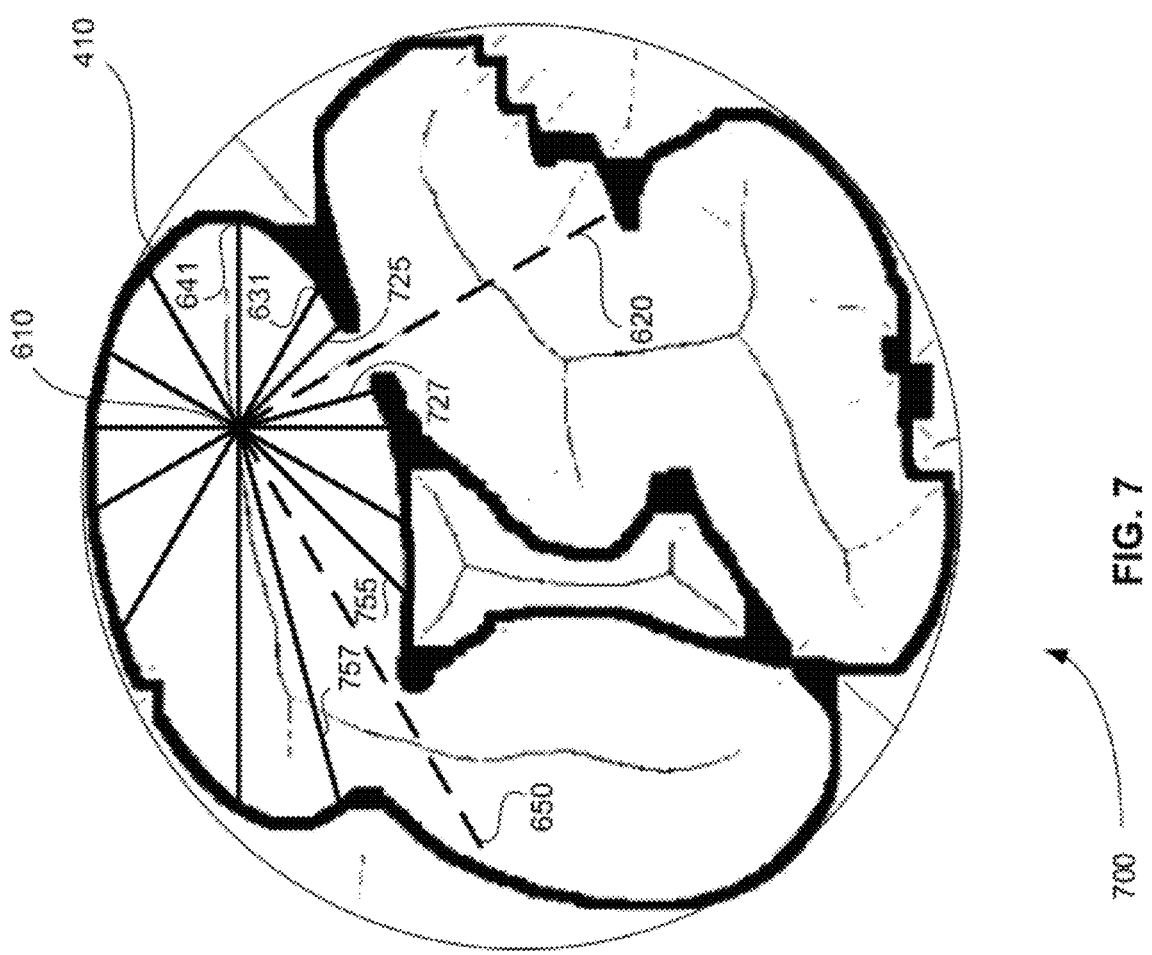
FIG. 7 is an exemplary combined image of the skeleton image of FIG. 2 and the dilated image of FIG. 4 that includes radial lines extending from a spine point to a boundary that are modified to approximate a pill shape in a merged or occluded area, in accordance with various embodiments.

FIG. 7 is an exemplary combined image 700 of the skeleton image of FIG. 2 and the dilated image of FIG. 4 that includes radial lines extending from a spine point 610 to a boundary that are modified to approximate a pill shape in a merged or occluded area, in accordance with various embodiments. In combined image 700 additional radial lines 725 and 727 are extended from spine point 610 closer to radial line 620 and additional radial lines 755 and 757 are extended from spine point 610 closer to radial line 650. Expected radial endpoints are calculated for each of these added radial lines. Finally, radial lines 620 and 650 are removed to produce a series of actual radial endpoints that correspond to boundary 410.

Figure 8:
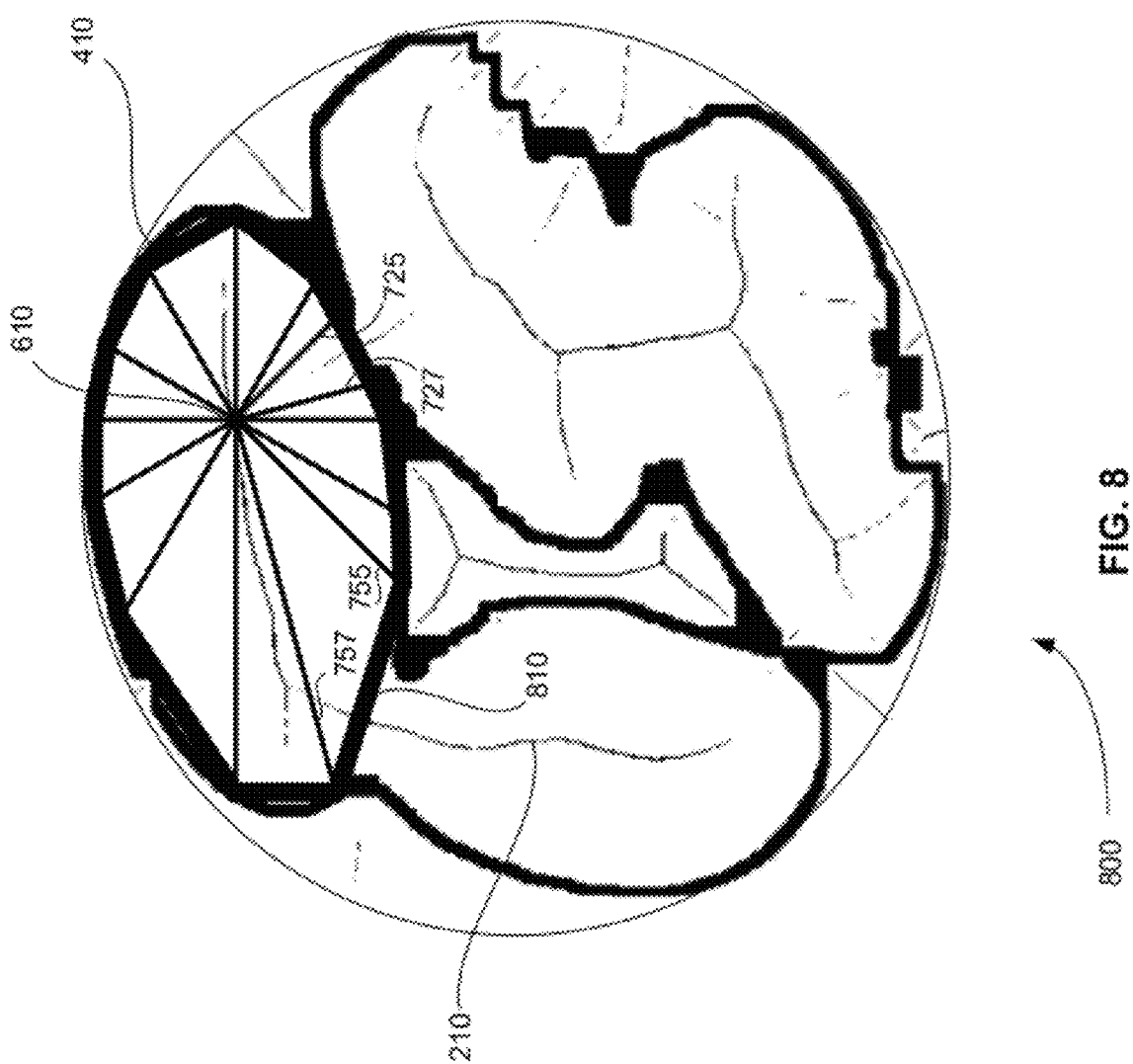
FIG. 8 is an exemplary combined image of the skeleton image of FIG. 2 and the dilated image of FIG. 4 that includes radial lines extending from a spine point to a boundary whose radial endpoints are connected to approximate a pill shape, in accordance with various embodiments.

FIG. 8 is an exemplary combined image 800 of the skeleton image of FIG. 2 and the dilated image of FIG. 4 that includes radial lines extending from a spine point 610 to a boundary whose radial endpoints are connected to approximate a pill shape, in accordance with various embodiments. The radial lines extending from spine point 610 include added radial lines 725, 727, 755, and 757. The actual radial endpoints for the radial lines extending from spine point 610 are used to calculate shape, color, and area features for pixels under the pill 110 in FIG. 1. The actual radial endpoints of the radial lines of combined image 800 of FIG. 8 are shown connected by lines producing illustrative approximate pill shape 810. A shape integration algorithm, such as a convex hull algorithm, can be used to create a shape mask, for example.

FIGS. 6-8 illustrate the process of determining radial endpoints for just one spine point of a captured image. In various embodiments, a set of radial endpoints is determined for each spine point in a captured image. An approximate shape and shape features are calculated from each set of radial endpoints for each spine point in the captured image. Approximate shapes that do not conform to the plurality of shape features based on shape proximity, for example, can be discarded as not representative of a predominant shape in the captured image. As a result, no a priori shape knowledge is required to determine the predominant shape.

In various embodiments, if a priori or application domain knowledge is available, this can also be used to determine if approximate shapes conform to the plurality of shape features. Application domain knowledge can include knowing that the shape of pills or capsules is almost always convex rather than concave, for example.

Figure 9:
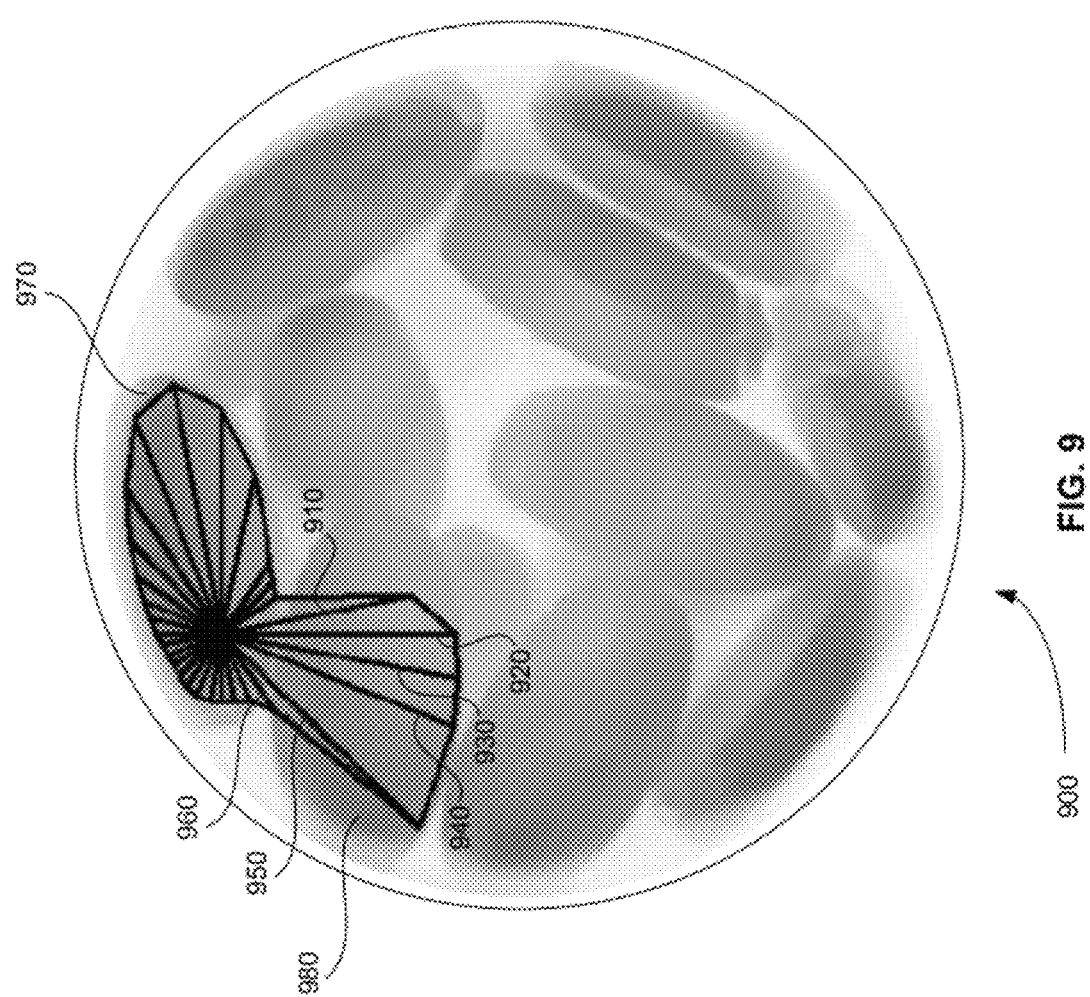
FIG. 9 is an exemplary negative image of radial lines extending from a spine point of a pill superimposed on a captured image that identify a merged or occluded area, in accordance with various embodiments.

FIG. 9 is an exemplary negative image 900 of radial lines extending from a spine point of a pill 970 superimposed on a captured image that identify a merged or occluded area, in accordance with various embodiments. In image 900, radial lines 910, 920, 930, 940, 950, and 960 identify a merged or occluded location between pills 970 and 980.

Figure 10:
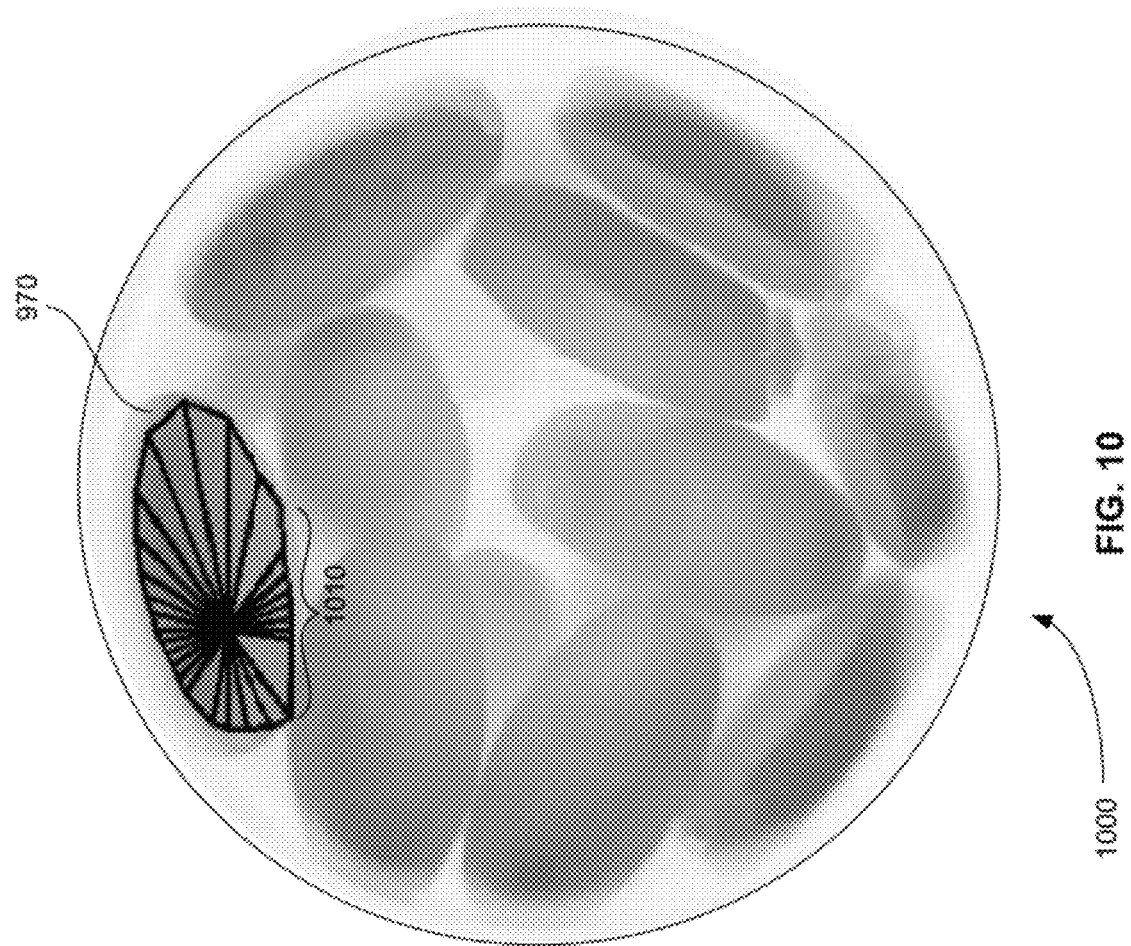
FIG. 10 is an exemplary negative image of radial lines extending from a spine point of a pill superimposed on the same captured image shown in FIG. 9 after the radial lines are modified to approximate a pill shape in the merged or occluded area, in accordance with various embodiments.

FIG. 10 is an exemplary negative image 1000 of radial lines extending from a spine point of a pill 970 superimposed on the same captured image shown in FIG. 9 after the radial lines are modified to approximate a pill shape in the merged or occluded area, in accordance with various embodiments. In image 1000, radial lines in area 1010 are removed from and added to approximate the shape of pill 970.

Figure 11:
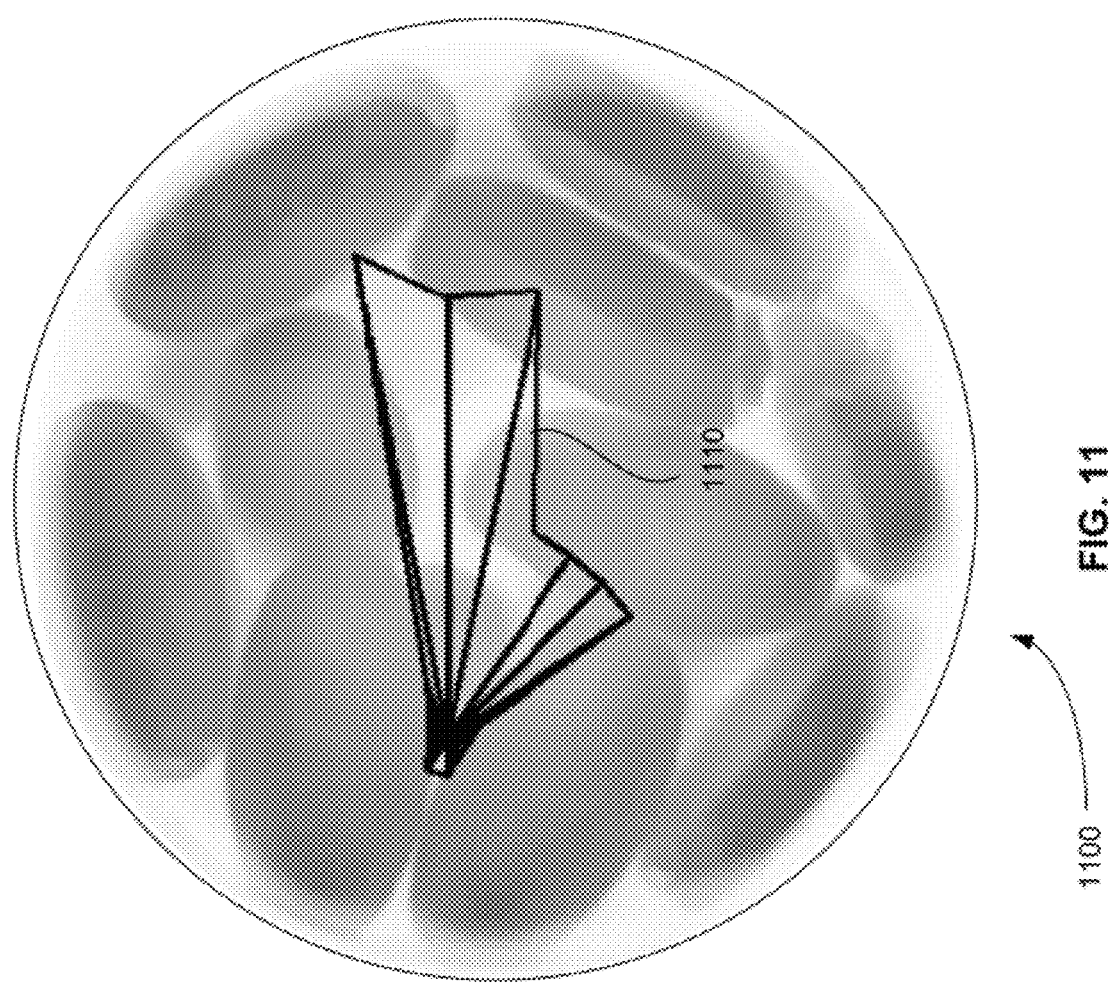
FIG. 11 is an exemplary negative image of radial lines extending from a spine point in an area between pills superimposed on a captured image, in accordance with various embodiments.

FIG. 11 is an exemplary negative image 1100 of radial lines extending from a spine point in an area between pills superimposed on a captured image, in accordance with various embodiments. Approximate shape 1110 is an example of the discontinuous shapes produced by spine points in the areas between pills. Such discontinuous shapes do not conform to the plurality of shape features based on shape proximity and are discarded as not being representative of a predominant shape in the captured image, for example.

Systems and Methods for Identifying a Discontinuity

As shown above, identifying a discontinuity in the boundary of a capsule or pill in a captured image of a prescription vial can be used to determine where the capsule or pill appears to be in contact or merged with other capsules or pills or where capsules or pills are occluded by some other artifact in the image. The fact that this technique can identify areas where capsules or pills that have substantially the same shape are merged or in contact, suggests that it works well for any collection of objects that share the same shape. The fact that this technique can also identify areas of a pill or capsule occluded by an artifact of a prescription vial and can identify areas between capsules or pills, suggests that it works equally as well for any collection of objects that have different shapes.

Figure 12:
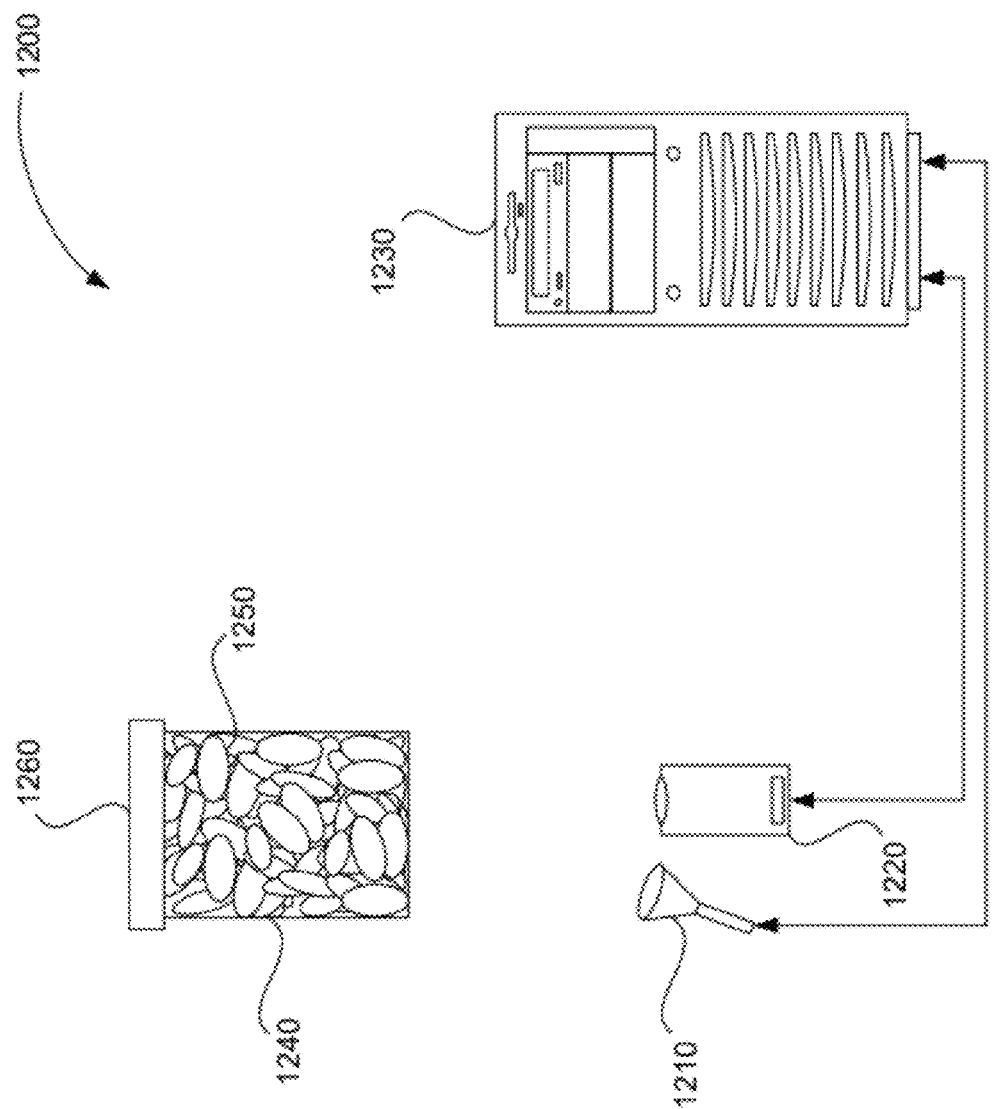
FIG. 12 is a schematic diagram showing a system for identifying a discontinuity in the boundary of an object in an image, in accordance with various embodiments.

FIG. 12 is a schematic diagram showing a system 1200 for identifying a discontinuity in the boundary of an object in an image, in accordance with various embodiments. System 1200 includes light source 1210, imaging device 1220, and processor 1230. Light source 1210 is, for example, an infrared light source or a visible light source. Light source 1210 illuminates one or more objects.

Imaging device 1220 is, for example, a digital camera. Imaging device 1220 captures an image of the one or more objects. In FIG. 12, the one or more objects illuminated by light source 1210 and imaged by imaging device 1220 are prescription vial 1240 and capsules or pills 1250, for example. Capsules or pills 1250 are illuminated and imaged through the bottom of prescription vial 1240, for example. Capsules or pills 1250 can also be illuminated and imaged through the sides of prescription vial 1240 or through the open cap 1260 of prescription vial 1240. One skilled in the art can appreciated that in various embodiments one or more objects can be illuminated and imaged with or without the use or inclusion of a container.

Processor 1230 is in communication with light source 1210 and imaging device 1220. This communication can include, but is not limited to, data communication or control information communication. Processor 1230 can include, but is not limited to, a computer, a microprocessor, an application specific integrated circuit, or any device capable of executing a series of instructions.

Processor 1230 performs a number of steps. Processor 1230 calculates one or more skeletons of the one or more objects in the captured image. Processor 1230 calculates one or more boundaries of the one or more objects in the captured image. Processor 1230 extends a plurality of radial lines from a spine point of a skeleton of the one or more skeletons to the one or more boundaries. Each radial line of the plurality of radial lines intersects a boundary of the one or more boundaries at a radial endpoint producing a plurality of radial endpoints.

For each radial endpoint of the plurality of radial endpoints, processor 1230 calculates an expected radial endpoint based on two or more neighboring radial endpoints. Processor 1230 calculates the expected radial endpoint based on the two or more neighboring radial endpoints using a curve fitting algorithm, for example. In various embodiments, the curve fitting algorithm is chosen based on application domain knowledge. In various embodiments, the curve fitting algorithm is chosen based on sensor information. Sensor information can include a possible shape found in a database through a comparison with data obtained by a sensor. A sensor can include, but is not limited to, an optical spectrometer that provides a spectral signature of an object to be compared with a database to determine a shape feature, for example.

If the difference between the radial endpoint and its expected radial endpoint exceeds a certain threshold, processor 1230 identifies a radial line including the radial endpoint as a location of discontinuity in the boundary of an object. The discontinuity identifies a merged or occluded area of the object, for example.

In various embodiments, if processor 1230 identifies a discontinuity, it attempts to remove the discontinuity. Processor 1230 can remove a discontinuity using one or more of the following steps, for example. These steps can be performed one or more times and in any order. In one step, processor 1230 removes the discontinuity by recalculating the expected radial endpoint of the radial line based on two or more next nearest neighboring radial endpoints. In another step, processor 1230 removes the discontinuity by adding one or more additional radial lines to the plurality of radial lines that extend from the spine point and recalculating the expected radial endpoint of the radial line based on radial endpoints of one or more additional radial lines. In another step, processor 1230 removes the discontinuity by removing the radial line identifying the discontinuity from the plurality of radial lines.

In various embodiments, after removing all discontinuities, processor 1230 calculates shape features of the object based on the plurality of radial endpoints. Shape features can include, but are not limited to, the shape of the boundary, the area of the boundary, or the color of the object. Processor 1230 calculates the shape features of the object based on the plurality of radial endpoints using a curve fitting algorithm, for example. As above, the curve fitting algorithm can be chosen based on application domain knowledge or sensor information, for example.

Figure 13:
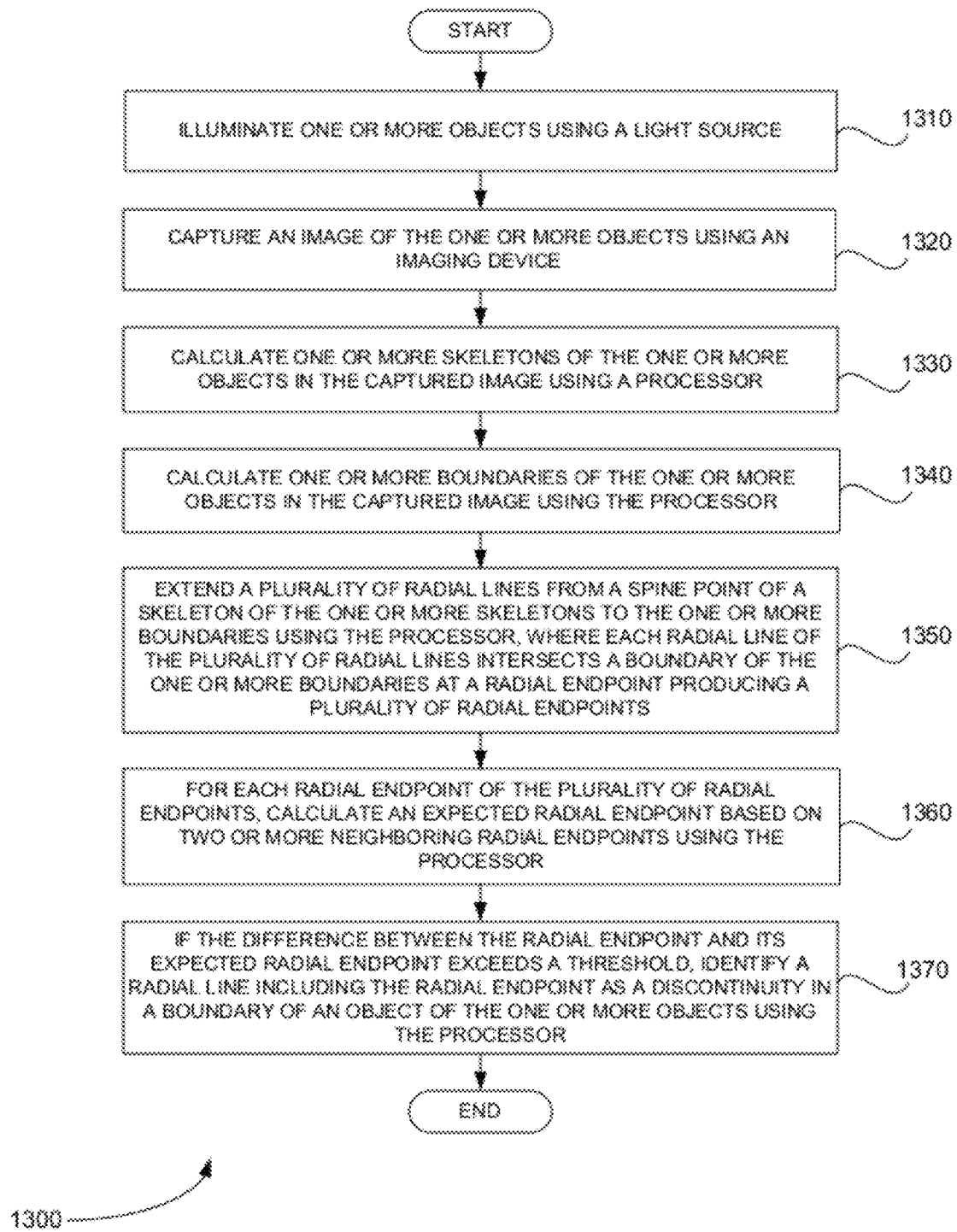
FIG. 13 is a flowchart showing a method for identifying a discontinuity in the boundary of an object in an image, in accordance with various embodiments.

FIG. 13 is a flowchart showing a method 1300 for identifying a discontinuity in the boundary of an object in an image, in accordance with various embodiments.

In step 1310 of method 1300, one or more objects are illuminated using a light source.

In step 1320, an image of the one or more objects is captured using an imaging device.

In step 1330, one or more skeletons of the one or more objects in the captured image are calculated using a processor.

In step 1340, one or more boundaries of the one or more objects in the captured image are calculated using the processor.

In step 1350, a plurality of radial lines is extended from a spine point of a skeleton of the one or more skeletons to the one or more boundaries using the processor. Each radial line of the plurality of radial lines intersects a boundary of the one or more boundaries at a radial endpoint producing a plurality of radial endpoints.

In step 1360, for each radial endpoint of the plurality of radial endpoints an expected radial endpoint is calculated based on two or more neighboring radial endpoints using the processor.

In step 1370, if the difference between the radial endpoint and its expected radial endpoint exceeds a threshold, a radial line including the radial endpoint is identified as a discontinuity in a boundary of an object of the one or more objects using the processor.

In accordance with various embodiments, instructions configured to be executed by a processor to perform a method are stored on a computer-readable storage medium. The computer-readable storage medium can be a device that stores digital information. For example, a computer-readable storage medium includes a compact disc read-only memory (CD-ROM) as is known in the art for storing software. The computer-readable storage medium is accessed by a processor suitable for executing instructions configured to be executed. The terms "instructions configured to be executed" and "instructions being executed" are meant to encompass any instructions that are ready to be executed in their present form (e.g., machine code) by a processor, or require further manipulation (e.g., compilation, decryption, or provided with an access code, etc.) to be ready to be executed by a processor.

In various embodiments, a computer program product includes a tangible computer-readable storage medium whose contents include a program with instructions being executed on a processor so as to perform a method for identifying a discontinuity in the boundary of an object in an image. This method is performed by a system of distinct software modules.

Figure 14:
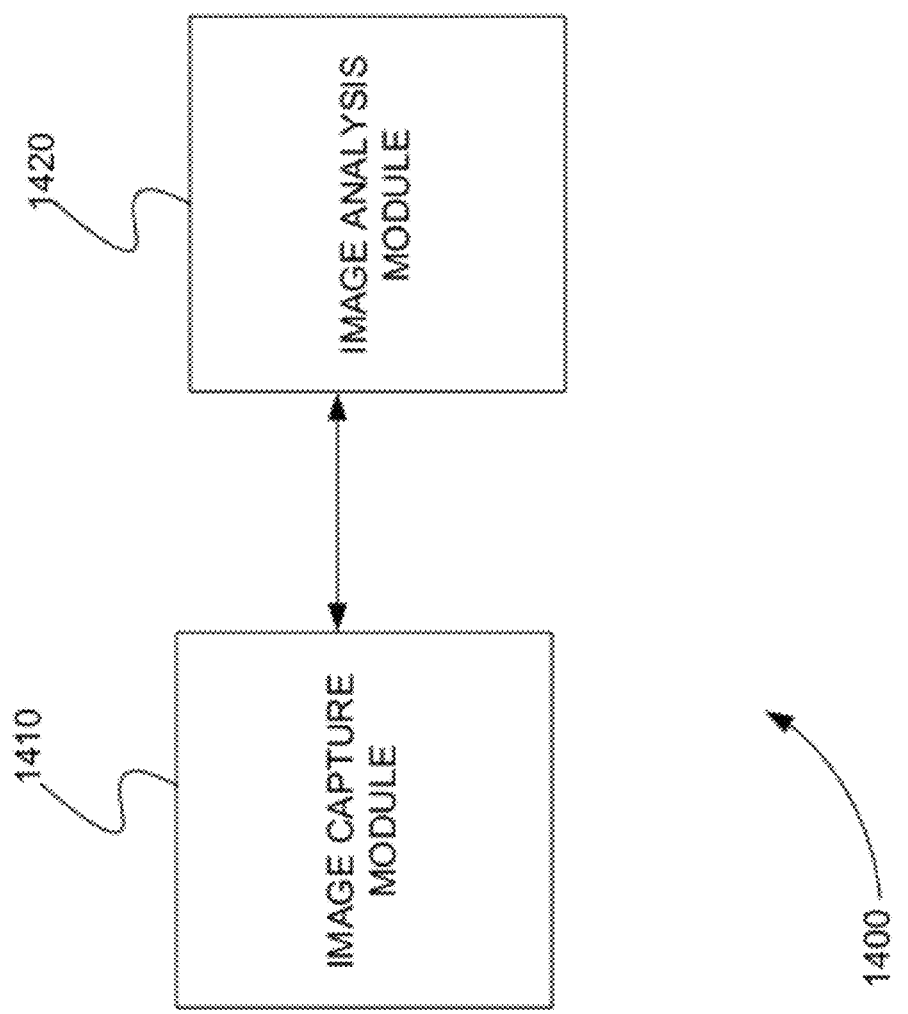
FIG. 14 is a schematic diagram of a system of distinct software modules that performs a method for identifying a discontinuity in the boundary of an object in an image, in accordance with various embodiments.

FIG. 14 is a schematic diagram of a system 1400 of distinct software modules that performs a method for identifying a discontinuity in the boundary of an object in an image, in accordance with various embodiments. System 1400 includes image capture module 1410 and image analysis module 1420. Image capture module 1410 receives a captured image of one or more objects illuminated by a light source from an imaging device.

Image analysis module 1420 performs a number of steps. Image analysis module 1420 calculates one or more skeletons of the one or more objects in the captured image. Image analysis module 1420 calculates one or more boundaries of the one or more objects in the captured image. Image analysis module 1420 extends a plurality of radial lines from a spine point of a skeleton of the one or more skeletons to the one or more boundaries. Each radial line of the plurality of radial lines intersects a boundary of the one or more boundaries at a radial endpoint producing a plurality of radial endpoints. Image analysis module 1420 calculates for each radial endpoint of the plurality of radial endpoints an expected radial endpoint based on two or more neighboring radial endpoints. If the difference between the radial endpoint and its expected radial endpoint exceeds a threshold, Image analysis module 1420 identifies a radial line including the radial endpoint as a discontinuity in a boundary of an object of the one or more objects.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for identifying a discontinuity in the boundary of an object in an image, comprising:
   a light source that illuminates one or more objects;
   an imaging device that captures an image of the one or more objects;
   a processor in communication with the light source and the imaging device that
      calculates one or more skeletons of the one or more objects in the captured image,
      calculates one or more boundaries of the one or more objects in the captured image,
      extends a plurality of radial lines from a spine point of a skeleton of the one or more skeletons to the one or more boundaries, wherein each radial line of the plurality of radial lines intersects a boundary of the one or more boundaries at a radial endpoint producing a plurality of radial endpoints,
      calculates for each radial endpoint of the plurality of radial endpoints an expected radial endpoint based on two or more neighboring radial endpoints, and
      if the difference between the each radial endpoint and its expected radial endpoint exceeds a threshold, identifies a radial line including the each radial endpoint as a discontinuity in a boundary of an object of the one or more objects.

2. The system of claim 1, wherein the discontinuity identifies a merged or occluded area of the object.

3. The system of claim 1, wherein the processor calculates an expected radial endpoint based on two or more neighboring radial endpoints using a curve fitting algorithm.

4. The system of claim 3, wherein the curve fitting algorithm is chosen based on application domain knowledge.

5. The system of claim 3, wherein the curve fitting algorithm is chosen based on sensor information.

6. The system of claim 1, wherein the processor further removes the discontinuity in the boundary of the object.

7. The system of claim 6, wherein the processor removes the discontinuity by recalculating the expected radial endpoint of the radial line based on two or more next nearest neighboring radial endpoints.

8. The system of claim 6, wherein the processor removes the discontinuity by adding one or more additional radial lines to the plurality of radial lines that extend from the spine point and recalculating the expected radial endpoint of the radial line based on radial endpoints of one or more additional radial lines.

9. The system of claim 6, wherein the processor removes the discontinuity by removing the radial line from the plurality of radial lines.

10. The system of claim 6, wherein the processor calculates shape features of the object based on the plurality of radial endpoints.

11. The system of claim 10, wherein the processor calculates the shape features of the object based on the plurality of radial endpoints using a curve fitting algorithm.

12. The system of claim 3, wherein the curve fitting algorithm is chosen based on application domain knowledge.

13. The system of claim 3, wherein the curve fitting algorithm is chosen based on sensor information.

14. A method for identifying a discontinuity in the boundary of an object in an image, comprising:
    illuminating one or more objects using a light source;
    capturing an image of the one or more objects using an imaging device;
    calculating one or more skeletons of the one or more objects in the captured image using a processor;
    calculating one or more boundaries of the one or more objects in the captured image using the processor;
    extending a plurality of radial lines from a spine point of a skeleton of the one or more skeletons to the one or more boundaries using the processor, wherein each radial line of the plurality of radial lines intersects a boundary of the one or more boundaries at a radial endpoint producing a plurality of radial endpoints;
    calculating for each radial endpoint of the plurality of radial endpoints an expected radial endpoint based on two or more neighboring radial endpoints using the processor; and
    if the difference between the each radial endpoint and its expected radial endpoint exceeds a threshold, identifying a radial line including the each radial endpoint as a discontinuity in a boundary of an object of the one or more objects using the processor.

15. The method of claim 14, wherein further comprising removing the discontinuity in the boundary of the object using the processor.

16. The method of claim 15, wherein removing the discontinuity comprises recalculating the expected radial endpoint of the radial line based on two or more next nearest neighboring radial endpoints.

17. The method of claim 15, wherein removing the discontinuity comprises adding one or more additional radial lines to the plurality of radial lines that extend from the spine point and recalculating the expected radial endpoint of the radial line based on radial endpoints of one or more additional radial lines.

18. The method of claim 15, wherein removing the discontinuity comprises removing the radial line from the plurality of radial lines.

19. The method of claim 15, further comprising calculating shape features of the object based on the plurality of radial endpoints using the processor.

20. A computer program product, comprising a tangible computer-readable storage medium whose contents include a program with instructions being executed on a computer system so as to perform a method for identifying a discontinuity in the boundary of an object in an image, the method comprising:
    providing a system, wherein the system comprises distinct software modules, and wherein the distinct software modules comprise an image capture module and an image analysis module;
    receiving a captured image of one or more objects illuminated by a light source from an imaging device using the image capture module;
    calculating one or more skeletons of the one or more objects in the captured image using the image analysis module;
    calculating one or more boundaries of the one or more objects in the captured image using the image analysis module;
    extending a plurality of radial lines from a spine point of a skeleton of the one or more skeletons to the one or more boundaries using the image analysis module, wherein each radial line of the plurality of radial lines intersects a boundary of the one or more boundaries at a radial endpoint producing a plurality of radial endpoints;
    calculating for each radial endpoint of the plurality of radial endpoints an expected radial endpoint based on two or more neighboring radial endpoints using the image analysis module; and
    if the difference between the each radial endpoint and its expected radial endpoint exceeds a threshold, identifying a radial line including the each radial endpoint as a discontinuity in a boundary of an object of the one or more objects using the image analysis module.

* * * * *